(12) United States Patent
Hiranuma et al.

(10) Patent No.: US 9,429,519 B2
(45) Date of Patent: Aug. 30, 2016

(54) FLUORESCENT LIGHT DETECTION DEVICE

(71) Applicant: Nippon Sheet Glass Company, Limited, Minato-ku, Tokyo (JP)

(72) Inventors: Yuji Hiranuma, Minato-ku (JP); Ikuto Oyama, Minato-ku (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 105 days.

(21) Appl. No.: 14/188,127

(22) Filed: Feb. 24, 2014

(65) Prior Publication Data

US 2014/0239193 A1    Aug. 28, 2014

(30) Foreign Application Priority Data

Feb. 25, 2013   (JP) .................................. 2013-035016

(51) Int. Cl.
*F21V 9/16*   (2006.01)
*G01N 21/64*   (2006.01)

(52) U.S. Cl.
CPC .......... *G01N 21/643* (2013.01); *G01N 21/645* (2013.01); *G01N 2201/08* (2013.01)

(58) Field of Classification Search
CPC ................... G01N 21/645; G01N 2021/6484; G01N 2021/6434; G01N 2021/6463
See application file for complete search history.

(56) References Cited

U.S. PATENT DOCUMENTS

| 8,263,945 | B2* | 9/2012 | Fukuzawa | ............ G01N 21/645 250/458.1 |
| 2003/0091294 | A1* | 5/2003 | Sasaki et al. | .................... 385/71 |
| 2004/0181148 | A1* | 9/2004 | Uchiyama et al. | ........... 600/425 |
| 2007/0035818 | A1* | 2/2007 | Bahatt et al. | ................. 359/366 |
| 2008/0293154 | A1* | 11/2008 | Makiuchi | ...................... 436/172 |
| 2008/0315118 | A1* | 12/2008 | Anraku | ..................... G01J 3/02 250/458.1 |
| 2009/0153852 | A1* | 6/2009 | Rensen | ......................... 356/300 |
| 2010/0210952 | A1* | 8/2010 | Taira et al. | ................... 600/476 |

FOREIGN PATENT DOCUMENTS

JP   2005-030830 A   2/2005

* cited by examiner

*Primary Examiner* — David J Makiya
*Assistant Examiner* — Kenneth J Malkowski
(74) *Attorney, Agent, or Firm* — Sughrue Mion, PLLC

(57) ABSTRACT

A fluorescent light detection device includes: an excitation light source; an excitation light fiber; a fluorescent light fiber; a detector configured to receive the fluorescent light emitted from the fluorescent light fiber; a retention member configured to retain the fibers so that an emitting end face of the excitation light fiber and an incident end face of the fluorescent light fiber are located at close proximity; an excitation light selection filter provided in contact with the emitting end face; and a fluorescent light selection filter provided in contact with the incident end face. The excitation light emitted from the emitting end face irradiates a test object via the excitation light selection filter and the fluorescent light produced by the test object is incident on the incident end face via the fluorescent light selection filter.

5 Claims, 8 Drawing Sheets

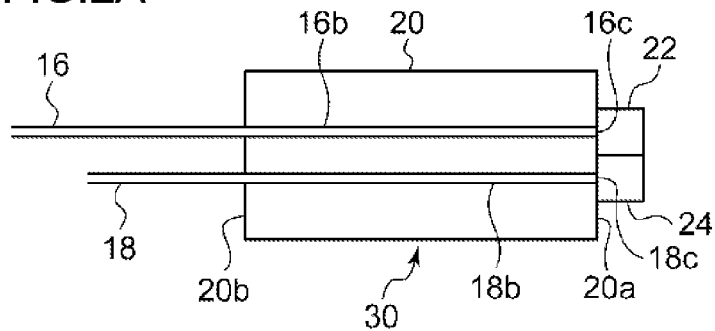
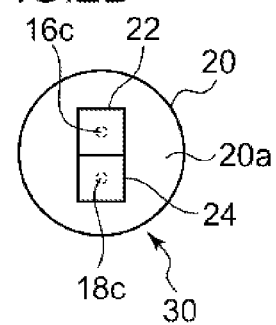
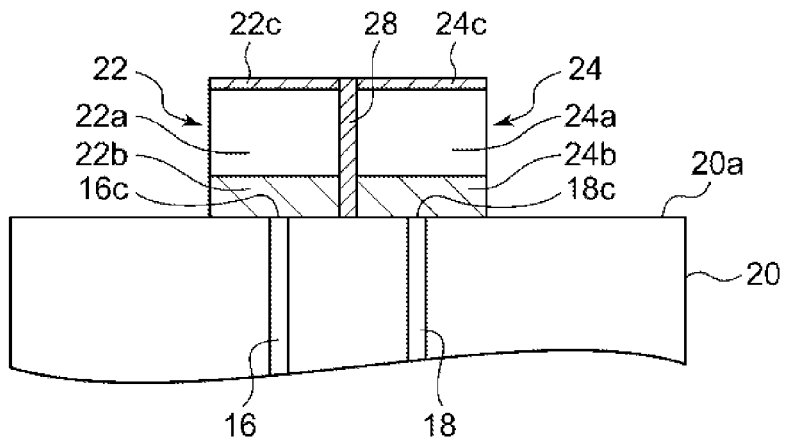
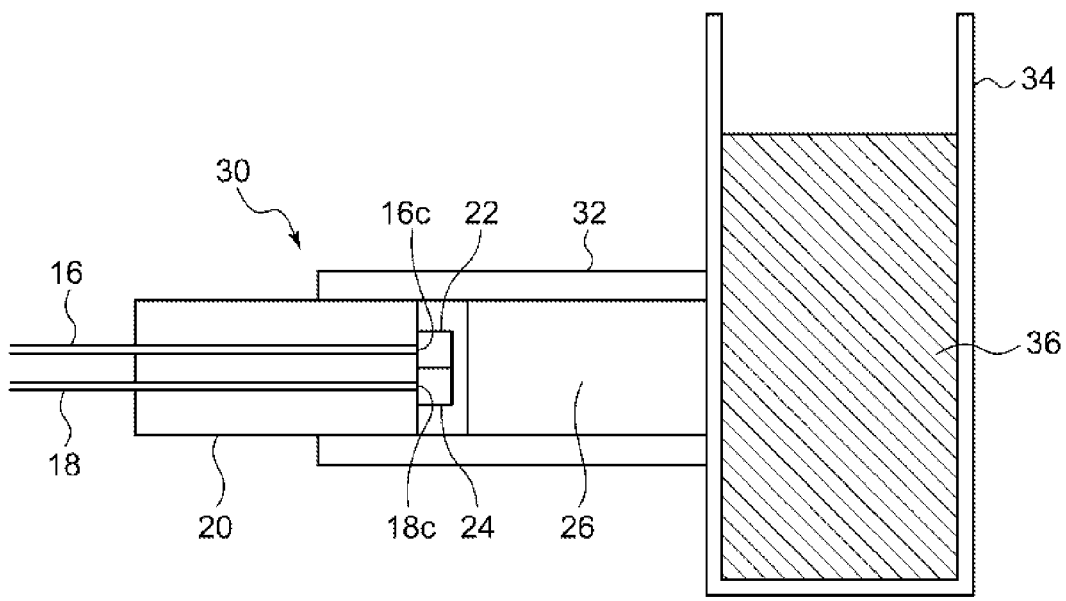

FLUORESCENT LIGHT DETECTION DEVICE

BACKGROUND OF THE INVENTION

1. Field of the Invention

The present invention relates to a fluorescent light detection device configured to irradiate a test object with an excitation light and detect a fluorescent light produced by the test object.

2. Description of the Related Art

A growing number of fluorescent light detection devices have been used in the field of life science. A fluorescent light detection device is easy-to-use and has high detection sensitivity. A fluorescent light detection device may sometimes be used in combination with an amplification step for efficient quantitative detection of nucleic acid such as DNA labeled by a fluorescent chemical substance.

For example, patent document 1 discloses a fluorescent light analysis optical module provided with an excitation light source configured to emit an excitation light having a main wavelength $\lambda 1$, a fluorescent light analysis optical multiplexer/demultiplexer configured to multiplex or demultiplex a fluorescent light having a main wavelength $\lambda 2$ produced by a sample irradiated with the excitation light via a probe; a detector configured to receive the fluorescent light transmitted through the fluorescent light analysis multiplexer/demultiplexer, a first light guide connecting the excitation light source and the optical multiplexer/demultiplexer, a second light guide connecting the probe to the optical multiplexer/demultiplexer, and a third light guide connecting the detector and the optical multiplexer/demultiplexer.
[patent document 1] JP2005-30830

The optical multiplexer/demultiplexer used in the invention described in cited document 1 is comprised of a first rod lens, a filter provided on the surface of the first rod lens, and a second rod lens secured to the filter. The optical multiplexer/demultiplexer is built by assembling these components serially and integrally. An optical multiplexer/demultiplexer of such a configuration tends to require a lot of effort and skill for positioning of the components in order to achieve highly efficient optical coupling using a rod lens and a filter. Therefore, the teachings disclosed in patent document 1 leaves room for improvement in terms of the cost.

SUMMARY OF THE INVENTION

The present invention addresses the issue discussed above and a purpose thereof is to provide an inexpensive fluorescent light detection device.

A fluorescent light detection device comprising: an excitation light source configured to emit excitation light; an excitation light fiber provided with an incident end face on which the excitation light from the excitation light source is incident and an emitting end face from which the excitation light is emitted; a fluorescent light fiber provided with an incident end face on which fluorescent light is incident and an emitting end face from which the fluorescent light is emitted; a detector configured to receive the fluorescent light emitted from the emitting end face of the fluorescent light fiber; a retention member configured to retain the excitation light fiber and the fluorescent light fiber so that the emitting end face of the excitation light fiber and the incident end face of the fluorescent light fiber are located at close proximity; an excitation light selection filter provided in contact with the emitting end face of the excitation light fiber; and a fluorescent light selection filter provided in contact with the incident end face of the fluorescent light fiber. The excitation light emitted from the emitting end face of the excitation light fiber irradiates a test object via the excitation light selection filter and the fluorescent light produced by the test object irradiated with the excitation light is incident on the incident end face of the fluorescent light fiber via the fluorescent light selection filter.

Each of the excitation light selection filter and the fluorescent light selection filter may be provided with a transparent base and a dielectric multilayer film formed on one of the surfaces of the transparent base. The dielectric multilayer film of the excitation light selection filter may be provided in contact with the emitting end face of the excitation light fiber, and the dielectric multilayer film of the fluorescent light selection filter may be provided in contact with the incident end face of the fluorescent light filter.

Each of the excitation light selection filter and the fluorescent light selection filter may further be provided with a antireflection film formed on the other surface of the transparent base.

The fluorescent light detection device may further comprise a light absorbing light shielding member provided between the excitation light selection filter and the fluorescent light selection filter.

Each of the excitation light selection filter and the fluorescent light selection filter may be provided with a transparent base and a diffractive optical element formed on one of the surface of the transparent base. The diffractive optical element of the excitation light selection filter may be provided in contact with the emitting end face of the excitation light fiber, and the diffractive optical element of the fluorescent light selection filter may be provided in contact with the incident end face of the fluorescent light fiber.

The fluorescent light detection device may further comprise an object lens provided to face the excitation light selection filter and the fluorescent light selection filter. The object lens may be a graded index rod lens.

The fluorescent light detection device may further comprise an excitation light collimating lens provided between the object lens and the excitation light selection filter; and a fluorescent light collimating lens provided between the object lens and the fluorescent light selection filter. The excitation light collimating lens and the fluorescent light collimating lens may be arranged such that the beam of excitation light does not overlap a range in which the fluorescent light is receivable.

The excitation light fiber and/or the fluorescent light fiber may be a plastic fiber.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIGS. 2A and 2B show the structure of the probe;

FIG. 2A is a sectional view of the probe 30 and FIG. 2B is a front view of the probe;

FIG. 3 shows the structure of the excitation light selection filter and the fluorescent light selection filter in further detail;

FIG. 4 shows the first exemplary embodiment of the present invention;

DETAILED DESCRIPTION OF THE INVENTION

The invention will now be described by reference to the preferred embodiments. This does not intend to limit the scope of the present invention, but to exemplify the invention.

A description will now be given of a fluorescent light detection device according to an embodiment of the present invention.

Figure 1:
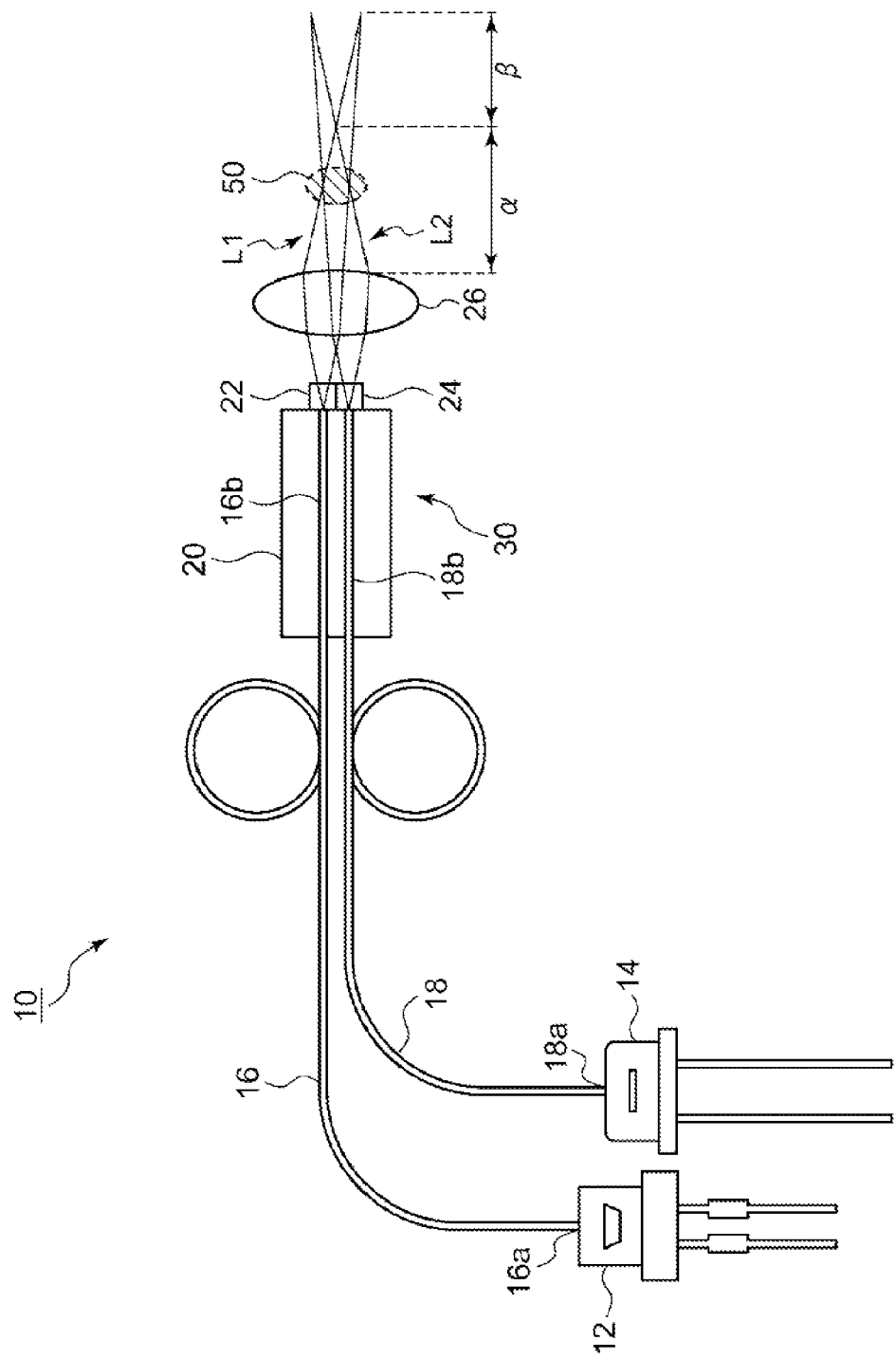
FIG. 1 shows a fluorescent light detection device according to the embodiment.

FIG. 1 shows a fluorescent light detection device 10 according to the embodiment. The fluorescent light detection device 10 is configured to irradiate a test object 50 with an excitation light and detect the fluorescent light produced by the test object 50.

As shown in FIG. 1, the fluorescent light detection device 10 is provided with an excitation light source 12 for emitting an excitation light, a probe 30 for irradiating the test object 50 with the excitation light and receiving the fluorescent light produced by the test object 50, a detector 14 for detecting the fluorescent light, an excitation light fiber 16 for propagating the excitation light from the excitation light source 12 to the probe 30, and a fluorescent light fiber 18 for propagating the fluorescent light from the probe 30 to the detector 14. Optionally, an object lens 26 may be provided between the probe 30 and the test object 50. For example, the object lens 26 may be a graded index rod lens.

The excitation light source 12 is configured to emit an excitation light to irradiate the test object 50. A light-emitting diode (LED) or a laser diode (LD) that includes a wavelength suitable to excite the test object 50 in an emitted light band may be used.

The detector 14 is configured to detect the fluorescent light produced by the test object 50 irradiated with the excitation light. A photodiode (PD), an avalanche photodiode (APD), or a photomultiplier tube (PMT) having a light-receiving band that covers the wavelength of the fluorescent light produced by the test object 50 may be used.

The excitation light fiber 16 is provided with an incident end face on which the excitation light from the excitation light source 12 is incident and an emitting end face from which the excitation light is emitted. An incident end 16a of the excitation light fiber 16 is connected to the excitation light source 12. The fluorescent light fiber 18 is provided with an incident end face on which the fluorescent light is incident and an emitting end face from which the fluorescent light is emitted. An emitting end 18a of the fluorescent light fiber 18 is connected to the detector 14.

FIGS. 2A and 2B show the structure of the probe 30. FIG. 2A is a sectional view of the probe 30 and FIG. 2B is a front view of the probe 30. As shown in FIGS. 2A and 2B, the probe 30 is comprised of an emitting end 16b of the excitation light fiber 16, an incident end 18b of the fluorescent light fiber 18, a retention member 20, an excitation light selection filter 22, and a fluorescent light selection filter 24.

The retention member 20 retains the emitting end 16b of the excitation light fiber 16 and the incident end 18b of the fluorescent light fiber 18 such that the emitting end face 16c of the excitation light fiber 16 and the incident end face 18c of the fluorescent light fiber 18 are located at close proximity. The retention member 20 is a cylindrical member or a polygonal column member. The retention member 20 has two through holes extending from an object end face 20a to the other end face 20b opposite to the object end face 20a or one through hole capable of accommodating the excitation light fiber and the fluorescent light fiber at the same time. The emitting end 16b of the excitation light fiber 16 is inserted into one of the through holes and retained therein. The incident end 18b of the fluorescent light fiber 18 is inserted into the other through hole and retained therein.

The retention member 20 may retain the emitting end 16b of the excitation light fiber 16 and the incident end 18b of the fluorescent light fiber 18 such that the emitting end face 16c of the excitation light fiber 16 and the incident end face 18c of the fluorescent light fiber 18 are flush. The retention member 20 may also be configured to ensure that the emitting end face 16c of the excitation light fiber 16, the incident end face 18c of the fluorescent light fiber 18, and the object end face 20a of the retention member 20 are flush.

The excitation light selection filter 22 is a filter configured to selectively transmit the excitation light. The excitation light selection filter 22 has a shape of a cylinder or a polygonal column. The excitation light selection filter 22 is provided on the object end face 20a of the retention member 20 so as to be in contact with the emitting end face 16c of the excitation light fiber 16.

The fluorescent light selection filter 24 is a filter configured to selectively transmit the fluorescent light produced by the test object 50. The fluorescent light selection filter 24 has a shape of a cylinder or a polygonal column. The fluorescent light selection filter 24 is provided on the object end face 20a of the retention member 20 so as to be in contact with the incident end face 18c of the fluorescent light fiber 18. The excitation light selection filter 22 and the fluorescent light selection filter 24 are provided adjacent to each other.

The shape and area of the surface of contact of the excitation light selection filter 22 and the fluorescent light selection filter 24 are defined to cover the entirety of the emitting end face 16c and the incident end face 18c, respectively. Since the excitation light selection filter 22 and the fluorescent light selection filter 24 are expensive, it is most economical to ensure that the contact surface of the excitation light selection filter 22 has the same shape and area as the fiber core on the emitting end face 16c and that the contact surface of the fluorescent light selection filter 24 has the same shape and area as the fiber core at the incident end face 18c. However, this would require highly precise mounting. It is therefore practical to ensure that the areas of the contact surface of the excitation light selection filter 22 and the fluorescent light selection filter 24 are several times (e.g., two to ten times) the areas of the emitting end face 16c and the incident end face 18c, respectively.

Referring back to FIG. 1, a description will be given of the operation of the fluorescent light detection device 10. The excitation light emitted by the excitation light source 12 is incident into the excitation light fiber 16 from the incident end face of the excitation light fiber 16. The excitation light propagated through the excitation light fiber 16 is emitted from the emitting end face 16c. The excitation light emitted from the emitting end face 16c is incident on the excitation light selection filter 22 and is emitted from the object surface via the excitation light selection filter 22. The excitation light emitted from the excitation light selection filter 22 irradiates the test object 50 directly or via the object lens 26.

The fluorescent light produced by the test object 50 irradiated with the excitation light is incident on the fluorescent light selection filter 24 at the object surface directly or via the object lens 26 and is emitted from the contact surface via the fluorescent light selection filter 24. The light emitted from the surface of contact of the fluorescent light selection filter 24 is incident on the fluorescent light fiber 18 via the incident end face 18c. The fluorescent light propagated through the fluorescent light fiber 18 is received by the detector 14 and converted into an electrical signal. The state of the test object 50 can be measured by analyzing the electrical signal.

It is favorable that the test object 50 is located in an area in which a beam of excitation light (indicated by L1 in FIG. 1) overlaps a range in which the fluorescent light can be received (referred to as fluorescent light receivable range and indicated by L2 in FIG. 1). Defining the end face of the fluorescent light fiber 18 facing the lens as a virtual light emitting end, the fluorescent light receivable range will be a range of a beam emitted from the virtual light emitting end with a fiber NA. FIG. 1 shows an area in which the beam of excitation light and the fluorescent light receivable range overlap as "α". If the test object 50 is located in an area further away from α (indicated by "β" in FIG. 1), the beam of excitation light and the fluorescent light receivable range do not overlap so that the fluorescent light cannot be suitably detected. This is because the focusing point of the excitation light and the virtual point of fluorescent light emission (corresponding to the image point focused by the object lens facing the end face of the fluorescent light fiber 18 facing the lens) are not aligned.

The irradiating light from the excitation light fiber 16 includes light of wavelengths outside the wavelength band suitable for excitation of the test object 50. According to the embodiment, the excitation light selection filter 22 is placed in contact with the emitting end face 16c of the excitation light fiber 16. It is therefore ensured that only the light transmitted from the excitation light selection filter 22 (i.e., the excitation light) irradiates the test object.

The light traveling toward the probe 30 from the test object 50 includes reflected light and scattering light from the excitation light and scattering light, in addition to the fluorescent light produced by the test object 50. The reflected light and scattering light from the excitation light and the scattering light produce noise in fluorescence detection in the detector 14. According to the embodiment, the fluorescent light selection filter 24 is placed in contact with the incident end face 18c of the fluorescent light fiber 18. It is therefore ensured that only the light transmitted through the fluorescent light selection filter 24 (i.e., the fluorescent light) is incident on the fluorescent light fiber 18. As a result, noise level in fluorescence detection in the detector 14 is reduced so that the fluorescent light is suitably detected.

The probe 30 of the fluorescent light detection device 10 according to the embodiment can be configured merely by mounting the excitation light selection filter 22 and the fluorescent light selection filter 24 so as to be in contact with the emitting end face 16c of the excitation light fiber 16 and the incident end face 18c of the fluorescent light fiber 18, respectively such that the excitation light fiber 16 and the fluorescent light fiber 18 are retained by the retention member 20. No works that require high level of precision (e.g., optical axis alignment) are required. Further, the optical multiplexer/demultiplexer as used in the teaching of patent document 1 described above is not necessary so that an inexpensive fluorescent light detection device 10 can be produced.

In the fluorescent light detection device 10 according to the embodiment, the excitation light selection filter 22 and the fluorescent light selection filter 24 are provided in contact with the emitting end face 16c of the excitation light fiber 16 and the incident end face 18c of the fluorescent light fiber 18, respectively. Hypothetically, the excitation light selection filter and the fluorescent light selection filter could be provided on the incident end face of the excitation light fiber 16 and the emitting end face of the fluorescent light fiber 18, respectively.

If the excitation light selection filter is provided between the incident end face of the excitation light fiber 16 and the light-emitting element of the excitation light source 12, the optical distance between the light-emitting element and the incident end face of the excitation light fiber 16 will be increased. This would require an additional lens for ensuring that the light from the light-emitting element is incident on the excitation light fiber 16 efficiently and would require additional cost. The optical distance between the fiber end face and the light-emitting element will be reduced by using a thin excitation light selection filter. This would, however, cause a different problem in that the filter may be warped. To provide the excitation light selection filter between the incident end face of the excitation light fiber 16 and the light-emitting element of the excitation light source 12, a dedicated excitation light source should be manufactured. Again, this would increase the cost. Further, in the case that the excitation light selection filter is provided at the incident end face of the excitation light fiber 16, the area of the excitation light selection filter tends to be increased. Since the excitation light selection filter becomes expensive, the impact on the cost is increased if the area is increased. The constituting elements related to the excitation light are discussed above. A similar discussion can be applied to the constituting elements related to the fluorescent light.

Since the fluorescent light detection device 10 according to the embodiment is configured such that the excitation light selection filter 22 and the fluorescent light selection filter 24 are provided on the emitting end face 16c of the excitation light fiber 16 and the incident end face 18c of the fluorescent light fiber 18, respectively, the aforementioned problem is not caused so that an inexpensive fluorescent light detection device 10 can be produced. In other words, since the excitation light selection filter and the fluorescent light selection filter are not provided on the incident end face of the excitation light fiber 16 and the emitting end face of the fluorescent light fiber 18, respectively, there is no need to provide an additional lens between the light-emitting element of the excitation light source 12 and the incident end 16a of the excitation light fiber 16 or between the light-receiving element of the detector 14 and the emitting end 18a of the fluorescent light fiber 18. In this embodiment, the excitation light source 12 and detector 14 that are inexpensive and commonly available can be used. According to the embodiment, the area of the excitation light selection filter 22 and the fluorescent light selection filter 24 is prevented from being increased so that the cost of the excitation light selection filter 22 and the fluorescent light selection filter 24 is prevented from being increased.

The type of the excitation light fiber 16 and the fluorescent light fiber 18 of the fluorescent light detection device 10 according to the embodiment is non-limiting. For example, a glass optical fiber, a quartz optical fiber, or a plastic optical fiber may be used. That an inexpensive plastic optical fiber can be used is a great advantage of the fluorescent light detection device 10 according to the embodiment. Characteristically, a plastic optical fiber produces fluorescent light from the fiber itself in the presence of excitation light due to its material characteristics. If a plastic optical fiber is used as an excitation light fiber in the absence of the excitation light selection filter on the emitting end face of the excitation light fiber, unlike the embodiment, and if the fluorescent light generated in the excitation light fiber irradiates the test object along with the excitation light, the fluorescent light may be incident on the fluorescent light fiber and detected by the detector. This may detract from the accuracy of analyzing fluorescent light. By way of contrast, even if a plastic optical fiber is used as the excitation light fiber 16 in the fluorescent light detection device 10 according to the embodiment, the fluorescent light generated in the excitation light fiber 16 is properly removed by the excitation light selection filter 22 placed in contact with the emitting end face 16c of the excitation light fiber 16. Therefore, a plastic optical fiber can be used in the embodiment without deteriorating the accuracy of analyzing fluorescent light. Therefore, an inexpensive fluorescent light detection device 10 can be produced.

FIG. 3 shows the structure of the excitation light selection filter 22 and the fluorescent light selection filter 24 in further detail. The excitation light selection filter 22 is comprised of a first transparent base 22a, a first dielectric multilayer film 22b formed on one of the surfaces of the first transparent base 22a, and a first antireflection film 22c formed on the other surface of the first transparent base 22a. The first dielectric multilayer film 22b is configured to selectively transmit the excitation light. The fluorescent light selection filter 24 is comprised of a second transparent base 24a, a second dielectric multilayer film 24b formed on one of the surfaces of the second transparent base 24a, and a second antireflection film 24c formed on the other surface of the second transparent base 24a. The second dielectric multilayer film 24b is configured to selectively transmit the fluorescent light.

As shown in FIG. 3, the excitation light selection filter 22 according to the embodiment is configured such that the first dielectric multilayer film 22b is provided in contact with the emitting end face 16c of the excitation light fiber 16. This allows the light emitted from the emitting end face 16c of the excitation light fiber 16 to immediately pass through the first dielectric multilayer film 22b so that the light outside the desired band is effectively removed.

The fluorescent light selection filter 24 is configured such that the second dielectric multilayer film 24b is provided in contact with the incident end face 18c of the fluorescent light fiber 18. This allows most of the light incident on the incident end face 18c of the fluorescent light fiber 18 to pass through the second dielectric multilayer film 24b so that the light outside the desired band is effectively removed.

The first antireflection film 22c provided on the other surface of the first transparent base 22a prevents surface reflection of the excitation light on the other surface. The first antireflection film 22c reduces the reflection light returning in the direction of the excitation light fiber 16 and so can increase the amount of excitation light irradiating the test object.

The second antireflection film 24c provided on the other surface of the second transparent base 24a prevents surface reflection of the fluorescent light on the other surface. The second antireflection film 24c reduces the reflection light returning in the direction of the test object 50 and so can increase the amount of fluorescent light detected.

As shown in FIG. 3, a light absorbing light shielding member 28 may be provided between the excitation light selection filter 22 and the fluorescent light selection filter 24. The light absorbing light shielding member 28 is provided in contact with the lateral surface of the first transparent base 22a and the lateral surface of the second transparent base 24a. By providing the light absorbing light shielding member 28, the stray light in the first transparent base 22a is prevented from entering the second transparent base 24a and the stray light in the second transparent base 24a is prevented from entering the first transparent base 22a. In other words, isolation characteristics between the excitation light selection filter 22 and the fluorescent light selection filter 24 can be maintained. The light absorbing light shielding member 28 may be formed of resin such as black polyacetal resin that does not emit fluorescent light.

The filters described above are being formed of a dielectric multilayer film. Alternatively, a diffractive optical element may be used to form the filters. In other words, the excitation light selection filter 22 and the fluorescent light selection filter 24 may be comprised of a transparent base and a diffractive optical element formed on one of the surfaces of transparent base. In this case, the diffractive optical element of the excitation light selection filter 22 is provided in contact with the emitting end face 16c of the excitation light fiber 16. The diffractive optical element of the fluorescent light selection filter 24 is provided in contact with the incident end face 18c of the fluorescent light fiber 18.

In this embodiment, the first transparent base 22a forming the base of the excitation light selection filter 22 and the second transparent base 24a forming the base of the fluorescent light selection filter 24 are desirably formed of a substance that does not substantially generate fluorescent light when irradiated with excitation light. Examples of such substance include optical glass such as BK7, quartz, etc.

A description will be given of exemplary embodiments. FIG. 4 shows the first exemplary embodiment of the present invention. In the first exemplary embodiment, a graded index rod lens is used as the object lens 26. The object lens 26 is fixed by a cylindrical fixing member 32 to the retention member 20 so as to face the excitation light selection filter 22 and the fluorescent light selection filter 24.

The type and characteristics of the constituting elements used in the first exemplary embodiment are listed below.

Excitation light source: LED, main wavelength $\lambda1=470$ nm

Excitation light fiber: quartz light fiber, SI200/250 (NA=0.3), core diameter=0.2 mm Retention member: capillary, outer diameter=1.8 mm, two parallel holes Excitation light selection filter: bandpass filter, pass band=455 nm to 480 nm Lens: graded index rod lens Fluorescent light fiber: quartz light fiber, SI200/250 (NA=0.3), core diameter=0.2 mm Fluorescent light selection filter: bandpass filter, pass band=515 nm between 540 nm, both inclusive Detector: photoelectric conversion device (PD)

Core-to-core distance between the excitation light fiber and the fluorescent light fiber=0.25 mm The fluorescent light from the sample is measured using the fluorescent light detection device according to the first exemplary embodiment. A fluorescent isothiocyanate (FITC) water solution is used as a sample that emits fluorescent light. The concentration of the FITC water solution used are 1, 10, 100, 300, 1000 nmol/L (nanomol/liter. The main wavelength $\lambda2$ of the fluorescent light emitted by the FITC is 520 nm. A sample 36 is placed in a quartz cell 34 of 10 mm×10 mm. As shown in FIG. 4, the end face of the probe 30 (i.e., the end face of the object lens 26) is arranged to abut the lateral surface of the quartz cell 34 and a value obtained by converting the electrical signal (electric current) output from the detector into a voltage via an amplifier is measured. A description will now be given of measurement results.

Figure 5:
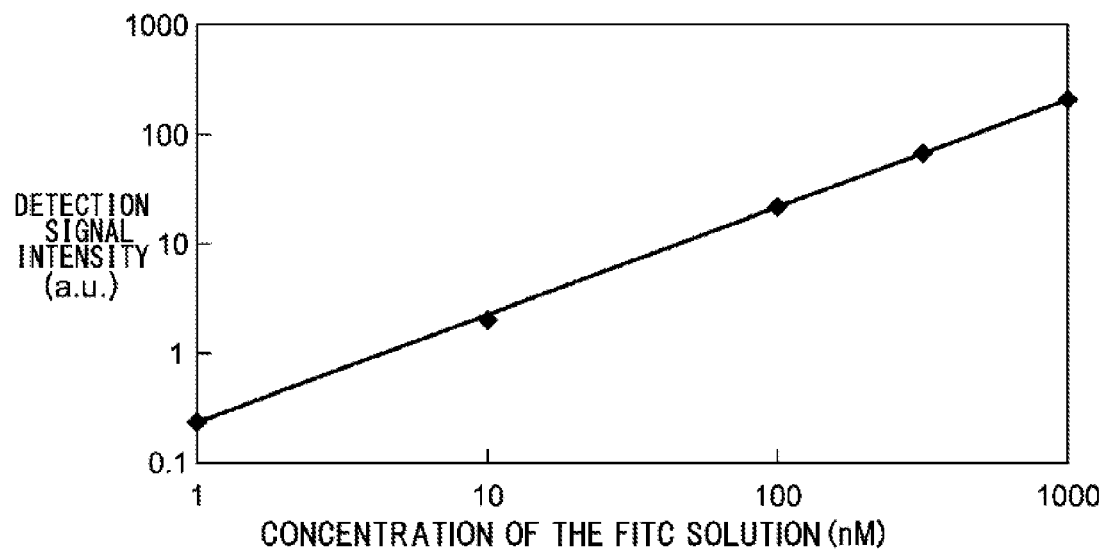
FIG. 5 shows measurement results showing the relationship between the concentration of the FITC solution and the detection signal intensity obtained by the fluorescent light device according to the first exemplary embodiment.

FIG. 5 shows measurement results showing the relationship between the concentration of the FITC water solution and the detection signal intensity obtained by the fluorescent light device according to the first exemplary embodiment. FIG. 5 demonstrates that the fluorescent light detection device according to the first exemplary embodiment maintains output linearity so that measurement of fluorescent light is possible.

Figure 6:
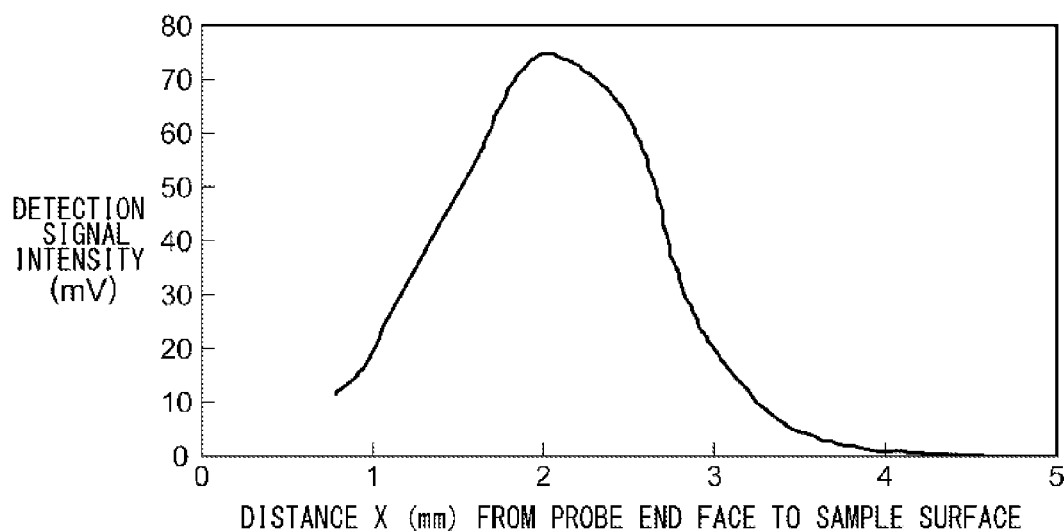
FIG. 6 shows measurement results showing the relationship between a distance X from the end face of the probe to the surface of the measurement sample and the detection signal intensity obtained by the fluorescent light detection device according to the first exemplary embodiment.
Figure 7:
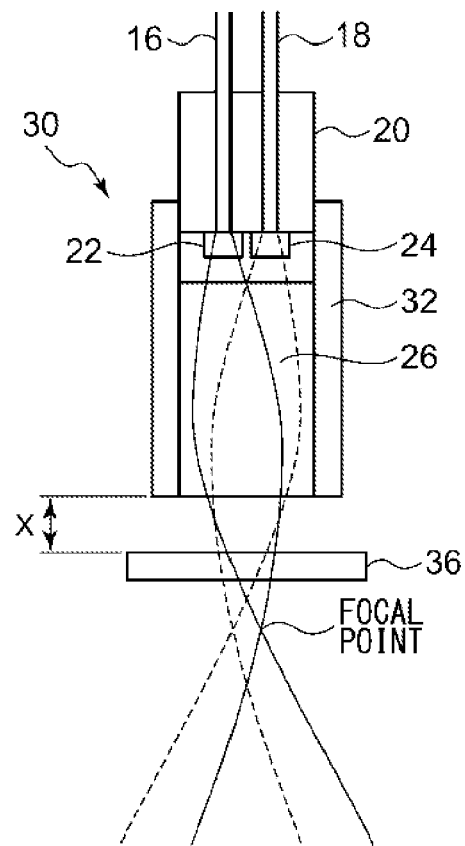
FIG. 7 shows a measurement system that provides the relationship shown in FIG. 6.

FIG. 6 shows measurement results showing the relationship between a distance X from the end face of the probe to the surface of the measurement sample and the detection signal intensity obtained by the fluorescent light detection device according to the first exemplary embodiment. FIG. 7 shows a measurement system by which the relationship shown in FIG. 6 is determined. In this measurement, a resin base is used as the sample 36 by which a fluorescent signal intensity substantially equal to the fluorescent signal intensity produced when the concentration of a "1000 nmol/L" FITC solution is measured. In this measurement, the thickness of the sample 36 is 1 mm. In this measurement system, the probe 30 focuses the excitation light. As shown in FIG. 7, the intensity of fluorescent light is detected while varying the distance X between the end face of the probe 30 and the surface of the measurement sample, and the measurement results shown in FIG. 6 are obtained. The measurement results of FIG. 6 demonstrate that fluorescent light can be measured by the measurement system shown in FIG. 7 and that the fluorescent light detection signal intensity depends on the distance X.

As described above with reference to FIG. 1, it is favorable that the test object is located in an area $\alpha$ in which a beam of excitation light overlaps a fluorescent light receivable range and that fluorescent light cannot be suitably detected in an area $\beta$ further away from the area $\alpha$. FIG. 6 shows that the signal intensity exhibits the maximum value at a position at which the intensity of excitation light irradiating the sample, the size, position, etc. of the spot of the focused beam, and the position of the sample are optimized. The figure also shows that displacement between the beam of excitation light and the fluorescent light receivable range occurs and the detection signal intensity drops radically as the distance X is increased.

Figure 8:
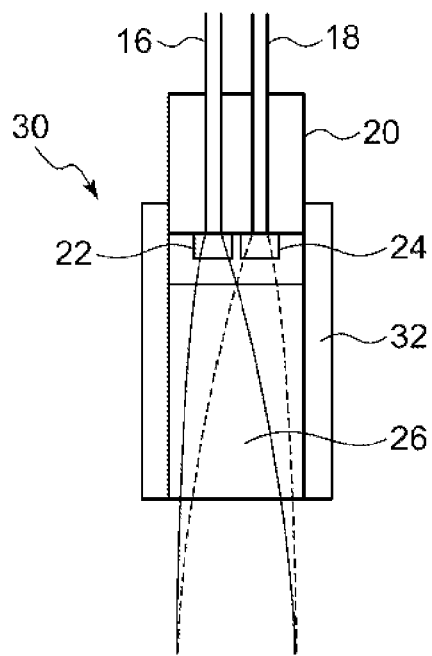
FIG. 8 shows the fluorescent light detection device according to the second exemplary embodiment of the present invention.
Figure 9:
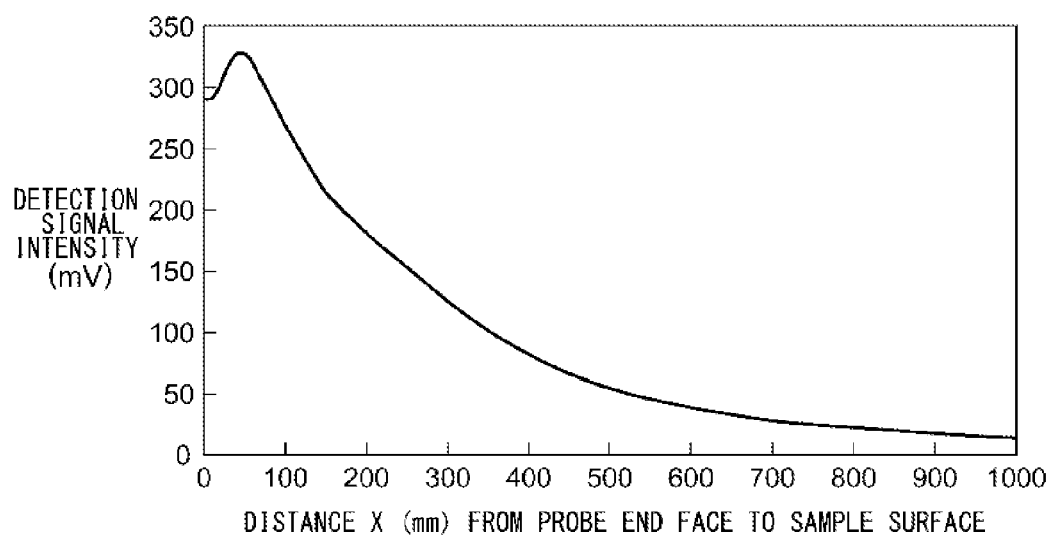
FIG. 9 shows measurement results showing the relationship between a distance X from the end face of the probe and the surface of the measurement sample and the detection signal intensity obtained by the fluorescent light detection device according to the second exemplary embodiment.

FIG. 8 shows the fluorescent light detection device according to the second exemplary embodiment. In the second exemplary embodiment, the probe 30 does not focus the excitation light. Instead, the probe 30 projects the excitation light to infinity. FIG. 9 shows measurement results showing the relationship between a distance X from the end face of the probe and the surface of the measurement sample and the detection signal intensity obtained by the fluorescent light detection device according to the second exemplary embodiment. FIG. 9 demonstrate that fluorescent light can be measured by the measurement system shown according to the second exemplary embodiment. The fluorescent light detection device according to the second embodiment has an advantage in that redundancy is secured as regards the distance X from the end face of the object lens 26.

Figure 10:
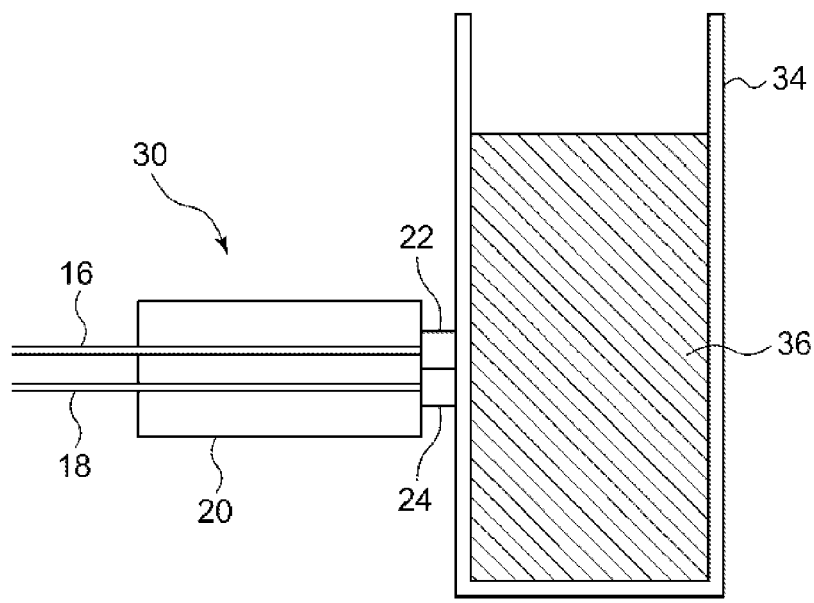
FIG. 10 shows the third exemplary embodiment of the present invention.

FIG. 10 shows the third exemplary embodiment of the present invention. The third exemplary embodiment differs from the first exemplary embodiment in that the object lens 26 is omitted.

The type and characteristics of the constituting elements used in the first exemplary embodiment are listed below.

Excitation light source: LED, main wavelength $\lambda1=470$ nm

Excitation light fiber: quartz light fiber, SI200/250 (NA=0.3), core diameter=0.2 mm Retention member: capillary, outer diameter=1.8 mm, two parallel holes Excitation light selection filter: bandpass filter, pass band=455 nm between 480 nm, both inclusive Fluorescent light fiber: quartz light fiber, SI200/250 (NA=0.3), core diameter=0.2 mm Fluorescent light selection filter: bandpass filter, pass band=515 nm between 540 nm, both inclusive Detector: photoelectric conversion device (PD)

Core-to-core distance between the excitation light fiber and the fluorescent light fiber=0.25 mm The fluorescent light from the sample is measured using the fluorescent light detection device according to the third exemplary embodiment described above. A fluorescent isothiocyanate (FITC) water solution is used as a sample that emits fluorescent light. The concentration of the FITC water solution used are 1, 10, 100, 300, 1000 nmol/L (nanomol/liter). The main wavelength $\lambda2$ of the fluorescent light emitted by the FITC is 520 nm. A sample 36 is placed in a quartz cell 34 of 10 mm×10 mm. As shown in FIG. 10, the end face of the probe 30 (i.e., the end faces of the excitation light selection filter 22 and the fluorescent light selection filter 24) are arranged to abut the lateral surface of the quartz cell 34 and a value obtained by converting the electrical signal (electric current) output from the detector into a voltage via an amplifier is measured. A description will now be given of measurement results.

Figure 11:
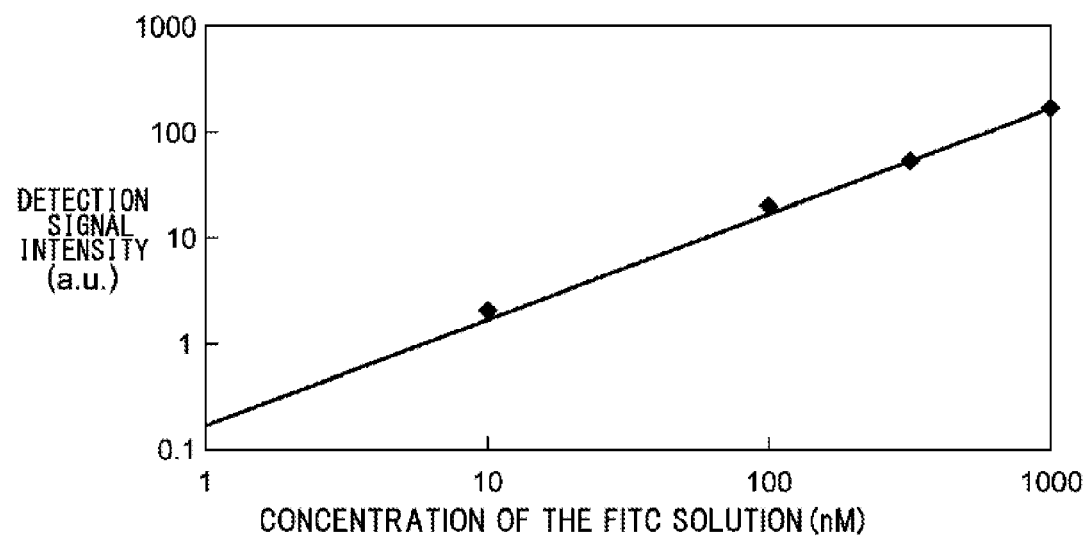
FIG. 11 shows measurement results showing the relationship between the concentration of the FITC solution and the detection signal intensity obtained by the fluorescent light device according to the third exemplary embodiment.

FIG. 11 shows measurement results showing the relationship between the concentration of the FITC water solution and the detection signal intensity obtained by the fluorescent light device according to the third exemplary embodiment. FIG. 11 demonstrates that the fluorescent light detection device according to the third maintains output linearity so that measurement of fluorescent light is possible.

Figure 12:
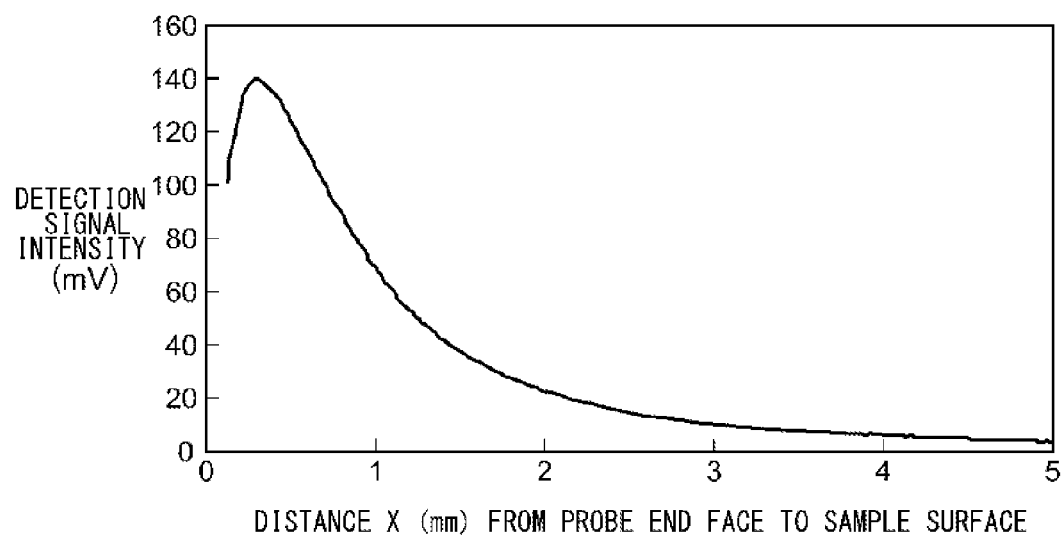
FIG. 12 shows measurement results showing the relationship between a distance X from the end face of the probe to the surface of the measurement sample and the detection signal intensity obtained by the fluorescent light detection device according to the third exemplary embodiment.
Figure 13:
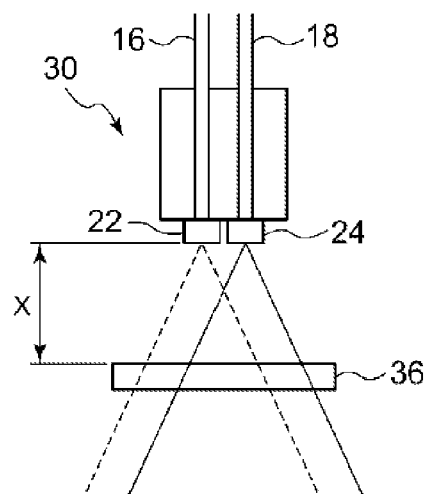
FIG. 13 shows a measurement system by which the relationship shown in FIG. 12 is determined.

FIG. 12 shows measurement results showing the relationship between a distance X from the end face of the probe to the surface of the measurement sample and the detection signal intensity obtained by the fluorescent light detection device according to the third exemplary embodiment. FIG. 13 shows a measurement system by which the relationship shown in FIG. 12 is determined. In this measurement, a resin base is used as the sample 36 by which a fluorescent signal intensity substantially equal to the fluorescent signal intensity produced when the concentration of a "1000 nmol/L" FITC solution is measured. In this measurement, the thickness of the sample 36 is 1 mm. FIG. 12 demonstrate that fluorescent light can be measured by the measurement system shown according to the third exemplary embodiment.

Figure 14A:
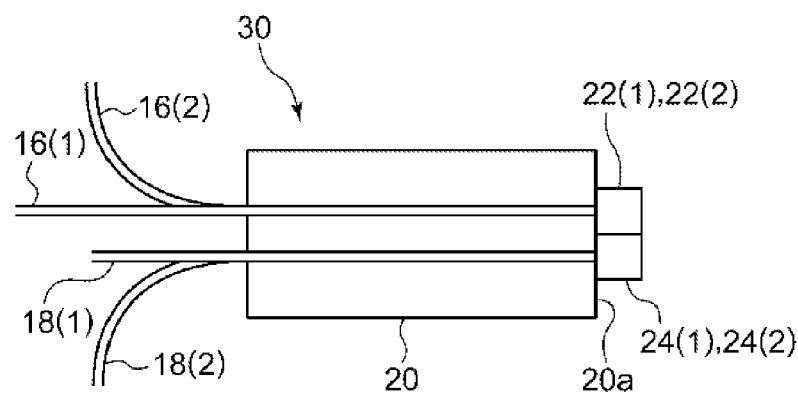
FIGS. 14A and 14B show a fluorescent light detection device according to the first alternative embodiment of the present invention.
Figure 14B:
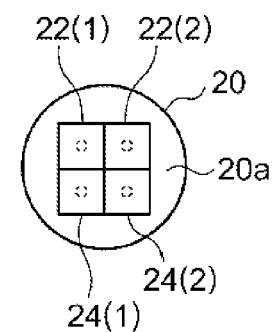

FIGS. 14A and 14B show a fluorescent light detection device according to the first alternative embodiment of the present invention. FIG. 14A is a sectional view of the probe 30, and FIG. 14b is a front view of the probe 30. The fluorescent light detection device 10 according to the first alternative embodiment covers a plurality of wavelengths. The fluorescent light detection device is provided with first and second excitation light sources (not shown), first and second detectors (not shown), a first excitation light fiber 16(1), a second excitation light fiber 16(2), a first fluorescent light fiber 18(1), a second fluorescent light fiber 18(2), a retention member 20 for supporting the ends of the fibers, a first excitation light selection filter 22(1) provided in contact with the emitting end face of the first excitation light fiber 16(1), a second excitation light selection filter 22(2) provided in contact with the emitting end face of the second excitation light fiber 16(2), a first fluorescent light selection filter 24(1) provided in contact with the incident end face of the first fluorescent light fiber 18(1), and a second fluorescent light selection filter 24(2) provided in contact with the incident end face of the second fluorescent light fiber 18(2). The configuration according to the first alternative embodiment that covers a plurality of wavelengths can also be used to produce an inexpensive fluorescent light detection device.

Figure 15:
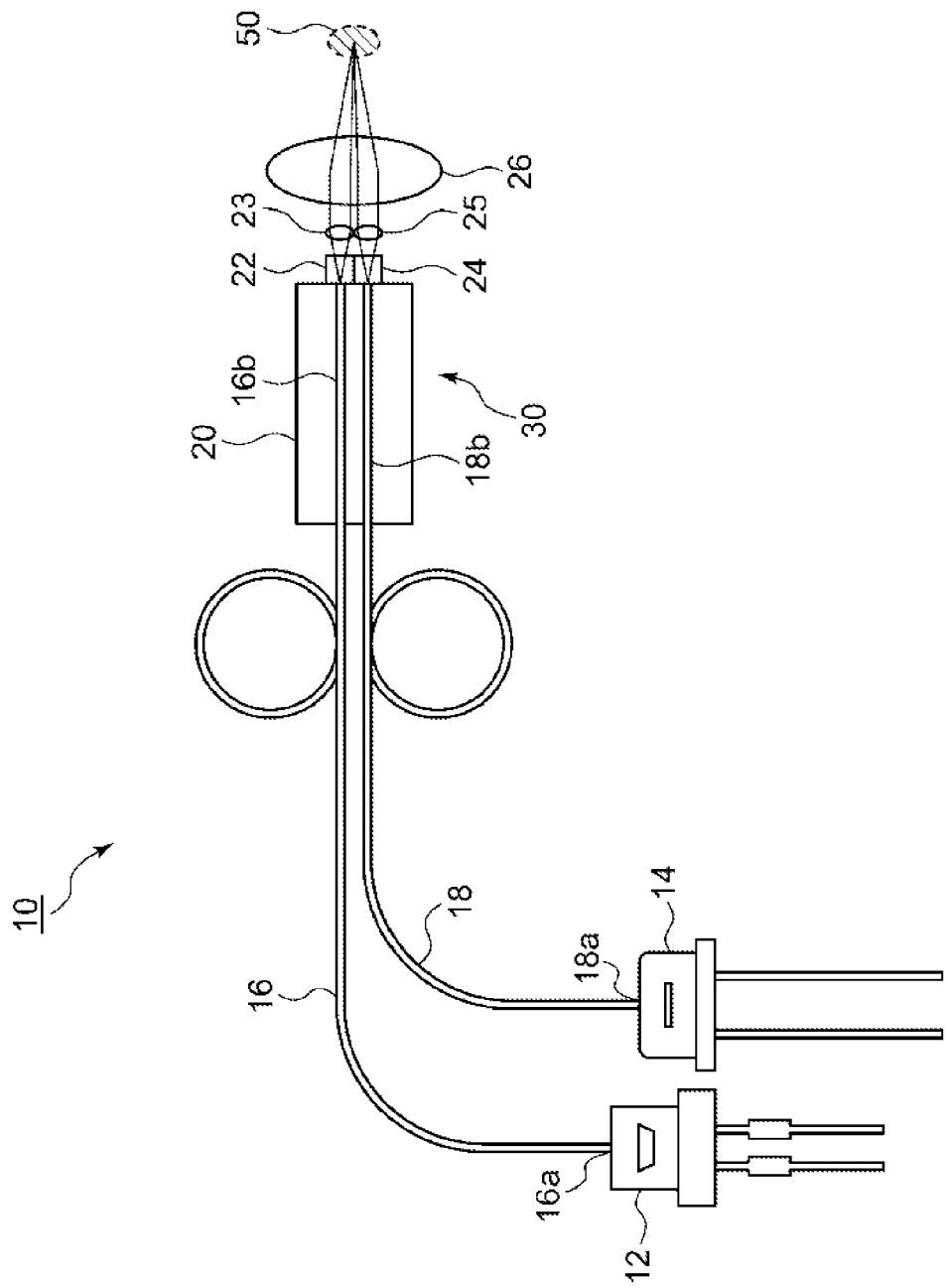
FIG. 15 shows a fluorescent light detection device according to the second alternative embodiment of the present invention.

FIG. 15 shows a fluorescent light detection device according to the second alternative embodiment of the present invention. Those constituting elements of the fluorescent light detection device 10 according to the second alternative embodiment that are identical to or corresponding to the elements of the fluorescent light detection device shown in FIG. 1 are denoted by the same reference numerals and associated descriptions will not be repeated.

In the fluorescent light detection device 10 according to the second alternative embodiment, an excitation light collimating lens 23 and a fluorescent light collimating lens 25 corresponding to the beams of excitation light and fluorescent light, respectively, and provided to ensure that the beam of excitation light does not overlap the fluorescent light receivable range are provided between the object lens 26 and the excitation light selection filter 22 and between the object lens 26 and the fluorescent light selection filter 24, respectively. In other words, the device is configured such that the end face of the excitation light fiber 16 and the concentrating point of the excitation light, and the point of fluorescent light emission and the end face of the fluorescent light fiber 18 are both finite conjugate relationship. The excitation light concentrating point and the fluorescent light emission point are substantially identical. By configuring the device as described above, the excitation light concentrates on the test object 50 located at a predetermined position in front of the object lens 26 and the fluorescent light emitted from the area can be efficiently guided to the fluorescent light fiber 18.

By configuring the device as described in the second alternative embodiment, concentration of the optical power on the test object 50 or the sample is enhanced, promoting emission of a larger amount of fluorescent light.

One of the problems in fluorescent light detectors and optical systems used therein is to reduce noise. One of the causes for noise is a phenomenon in which a fluorescent light detection optical system such as a fiber receives unexpected fluorescent light in an optical path of the excitation light. By configuring the optical system of the fluorescent light detection device 10 according to the second alternative embodiment such that the beam of excitation light and the fluorescent light receivable range do not overlap, the phenomenon in which unexpected fluorescent light is incident into the fluorescent light fiber is avoided so that the noise is reduced.

Described above is an explanation based on an exemplary embodiment. The embodiment is intended to be illustrative only and it will be obvious to those skilled in the art that various modifications to constituting elements and processes could be developed and that such modifications are also within the scope of the present invention.

What is claimed is:

1. A fluorescent light detection device comprising:
    an excitation light source configured to emit excitation light;
    an excitation light fiber provided with an incident end face on which the excitation light from the excitation light source is incident and an emitting end face from which the excitation light is emitted;
    a fluorescent light fiber provided with an incident end face on which fluorescent light is incident and an emitting end face from which the fluorescent light is emitted;
    a detector configured to receive the fluorescent light emitted from the emitting end face of the fluorescent light fiber;
    a retention member configured to retain the excitation light fiber and the fluorescent light fiber so that the emitting end face of the excitation light fiber and the incident end face of the fluorescent light fiber are located at close proximity;
    an excitation light selection filter provided in contact with the emitting end face of the excitation light fiber;
    a fluorescent light selection filter provided in contact with the incident end face of the fluorescent light fiber, and
    a light absorbing light shielding member provided between the excitation light selection filter and the fluorescent light selection filter,
    wherein the excitation light emitted from the emitting end face of the excitation light fiber irradiates a test object via the excitation light selection filter and the fluorescent light produced by the test object irradiated with the excitation light is incident on the incident end face of the fluorescent light fiber via the fluorescent light selection filter,
    wherein each of the excitation light selection filter and the fluorescent light selection filter is provided with a transparent base and a dielectric multilayer film formed on one of the surfaces of the transparent base, wherein the dielectric multilayer film of the excitation light selection filter is provided in contact with the emitting end face of the excitation light fiber, wherein the dielectric multilayer film of the fluorescent light selection filter is provided in contact with the incident end face of the fluorescent light filter, and wherein the light absorbing light shielding member is provided on a lateral surface of the transparent base.

2. The fluorescent light detection device according to claim 1, wherein each of the excitation light selection filter and the fluorescent light selection filter is further provided with a antireflection film formed on the other surface of the transparent base.

3. The fluorescent light detection device according to claim 1, wherein the excitation light fiber and/or the fluorescent light fiber is a plastic fiber.

4. The fluorescent light detection device according to claim 1, wherein an area of a contact surface of the excitation light selection filter is 2-10 times an area of the emitting end face of the excitation light fiber, and an area of a contact surface of the fluorescent light selection filter is 2-10 times an area of the incident end face of the fluorescent light fiber.

5. The fluorescent light detection device according to claim 1, wherein a beam of excitation light overlaps a fluorescent light receivable range.

* * * * *